(12) United States Patent
Fukuzumi

(10) Patent No.: US 7,166,554 B2
(45) Date of Patent: Jan. 23, 2007

(54) PHOTOCATALYST

(75) Inventor: Shunichi Fukuzumi, Toyonaka (JP)

(73) Assignee: Japan Science and Technology Agency, Kawaguchi (JP)

( * ) Notice: Subject to any disclaimer, the term of this patent is extended or adjusted under 35 U.S.C. 154(b) by 12 days.

(21) Appl. No.: 10/493,821

(22) PCT Filed: Sep. 4, 2002

(86) PCT No.: PCT/JP02/08972

§ 371 (c)(1),
(2), (4) Date: Apr. 28, 2004

(87) PCT Pub. No.: WO03/037510

PCT Pub. Date: May 8, 2003

(65) Prior Publication Data

US 2005/0003954 A1   Jan. 6, 2005

(30) Foreign Application Priority Data

Oct. 29, 2001   (JP)   ............................. 2001-331307

(51) Int. Cl.
*B01J 31/00*   (2006.01)
*B01J 23/00*   (2006.01)
*B01J 23/10*   (2006.01)

(52) U.S. Cl. ...................................... 502/150; 502/302
(58) Field of Classification Search ................ 502/150, 502/302
See application file for complete search history.

(56) References Cited

U.S. PATENT DOCUMENTS 6,720,458 B1 *   4/2004   Morikawa et al. ........... 568/436

FOREIGN PATENT DOCUMENTS

JP   58-183940 A   10/1983
JP   11-94796 A   4/1999

OTHER PUBLICATIONS

Shun'ichi Fukuzumi, "Kidorui Sakutai no Denshi Ido Shokubai Sayo, Kidorui Sakutai no Shin Tenkai", Heisei 7 Nendo Kenkyu Seika Hokokusho, 1996, pp. 265 to 268.

(Continued)

*Primary Examiner*—David Sample
*Assistant Examiner*—Patricia L. Hailey
(74) *Attorney, Agent, or Firm*—Birch, Stewart, Kolasch & Birch, LLP

(57) ABSTRACT

To provide a photocatalyst having a photocatalytic activity far higher than that of flavin, and being excellent in stability as a catalyst. A photocatalyst comprising a flavin-rare earth metal ion complex.

2 Claims, 9 Drawing Sheets

OTHER PUBLICATIONS

Kiyomi Yasui et al., "Hikari Denshi Ido Hanno ni okeru Kidorui Ion no Shokubai Sayo", Rave Earths, May 16, 1996, No. 28, pp. 324 to 325.

Shun'ichi Fukuzumi et al., "Efficient Catalysts of Rare-Earth Metal Ions in Photoinduced Electron-Transfer Oxidation of Benzyl Alcohols by a Flavin Analogue", J. Phys. Chem.A., Nov. 22, 2001, vol. 105, No. 46, pp. 10501 to 10510.

Shun'ichi Fukuzumi et al., "Photooxidation of Benzyl Alcohol Derivatives by Oxygen, Catalyzed by Protonated Flavin Analogues", Res. Chem. Intermed., 1999, vol. 25, No. 8, pp. 789 to 811, no month.

Shun'ichi Fukuzumi et al., "Protonated Pteridine and Flavin Analogues acting as Efficient and Substrate-selective Photocatalysts in Benzyl Alcohol Derivatives by Oxygen", J. Chem.Soc., Chem. Commun., 1989, No. 13, pp. 816 to 818, no month.

Shun'ichi Fukuzumi et al., "Flavin Analogue-Metal Ion Complexes Acting as Efficient Photcatalysts in the Oxidation of p-Methylbenzyl Alcohol by Oxygen under Irradiation with Visible Light"., J.Am. Chem.Soc., 1985, vol. 107, No. 11, pp. 3020 to 3027, no month.

* cited by examiner

R = CH₂(CHOCOMe)₃CH₂OCOMe

PHOTOCATALYST

TECHNICAL FIELD

The present invention relates to a photocatalyst. More specifically, the present invention relates to a photocatalyst having a high photocatalytic activity with little deactivation of catalytic activity, which can be suitably used as a high-activity, long-lifetime photooxidation catalyst. The photocatalyst is used, for instance, in the photooxidative reaction of benzyl alcohol or the like which is used as a chemical or the like.

BACKGROUND ART

Conventionally, there has been known that a flavin can be used as a photocatalyst in an oxidative reaction.

However, today, there has been earnestly desired the development of a photocatalyst having a photocatalytic activity far higher than that of a flavin, and being excellent in stability as a catalyst.

DISCLOSURE OF INVENTION

The present invention has been accomplished in view of the above-mentioned prior art, and an object of the present invention is to provide a photocatalyst having a photocatalytic activity far higher than that of flavin, and being excellent in stability as a catalyst.

The present invention relates to a photocatalyst comprising a flavin-rare earth metal ion complex.

BRIEF DESCRIPTION OF THE DRAWINGS

Each of FIG. 1(a)

BEST MODE FOR CARRYING OUT THE INVENTION

Figure 1:
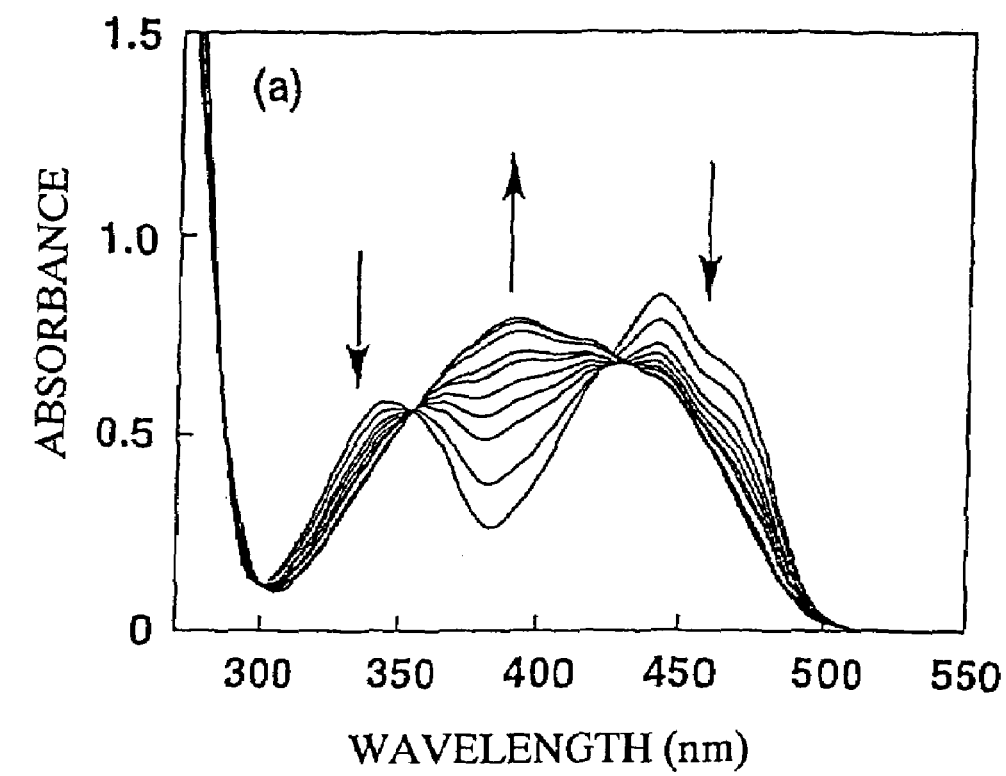
FIG. 1(b) is an electronic absorption spectrum of Fl ($1.0 \times 10^{-4}$ M) in the presence of various concentrations of $Sc^{3+}$ in MeCN at 298 K.
Figure 1:
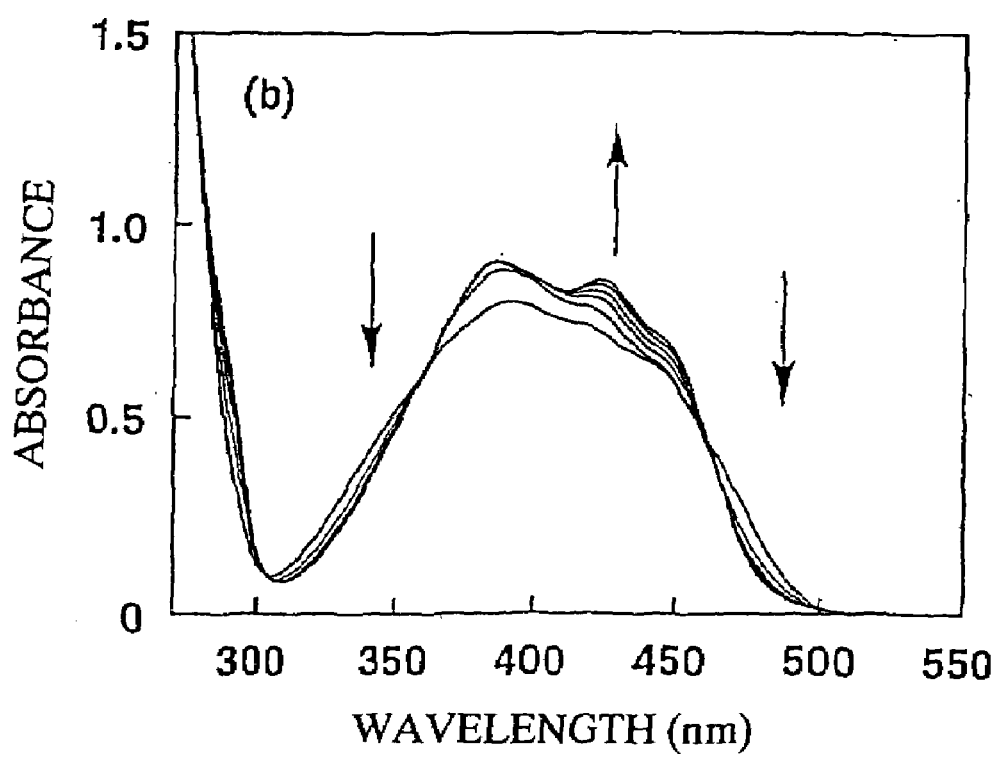

Flavoenzymes are a ubiquitous and structurally and functionally diverse class of oxidation-active proteins that use the isoalloxazine ring of flavins to mediate a variety of electron transfer processes over a wide range of redox potentials. The redox reactivity of flavins is modulated by the interaction with apoenzymes, that is affected by hydrogen-bonding, π-π stacking, donor-π interaction, conformational effects and coordination to metal ions.

The redox reactivity of flavins is most drastically changed by the photoexcitation as compared to the ground state. Therefore, photochemistry of flavoenzymes and flavin analogues has been the main subject of research in photocatalysts for the photobiological reduction processes.

The oxidation reactivity of the photoexcited states of flavins has been further modulated by coordination to metal ions. Divalent metal cations ($Mg^{2+}$, $Ca^{2+}$, $Sr^{2+}$, $Ba^{2+}$, $Zn^{2+}$ or $Cd^{2+}$) have been reported to be indispensable for the flavin-dependent photocleavage of RNA at particular base pairs via oxidative cleavage processes.

The effect of metal ions on the photocatalytic reactivity has also been studied using flavin analogues with the crown ether moiety as a binding site to metal ions.

Among metal ions, rare-earth metal ions have attracted interests as mild and selective Lewis acids in organic synthesis chemistry.

Trivalent rare-earth metal ($Sc^{3+}$, $Yb^{3+}$ and the like) trifluoromethanesulfonates [hereinafter referred to as triflates] have been utilized as Lewis acids in promoting various carbon-carbon bond forming reactions. In particular, scandium (III) triflate [hereinafter referred to as Sc(OTf)$_3$] is highly remarked due to its strong affinity to carbonyl oxygen.

However, there has not yet been reported on the effects of rare-earth metal ions on the oxidation reactivity of photoexcited states of flavins and the photocatalytic reactivity.

Incidentally, the photocatalyst of the present invention comprises a flavin-rare earth metal ion complex. The flavin as referred herein means flavin analogues. Among the flavin analogues, riboflavin-2',3',4',5'-tetraacetate (hereinafter referred to as "Fl") is preferable in the present invention. Fl has a characteristic of forming a 1:1 complex or 1:2 complex with a rare-earth metal ion.

The largest formation constants $K_1$ and $K_2$ for a complex of which molar ratio of Fl to $Sc^{3+}$ is 1:1 (1:1 complex of flavin with $Sc^{3+}$) and a complex of which molar ratio of Fl to $Sc^{3+}$ is 1:2 (1:2 complex of flavin with $Sc^{3+}$) are determined as $K_1=3.1 \times 10^4$ M$^{-1}$ and $K_2=1.4 \times 10^3$ M$^{-1}$, respectively.

By the complexation of Fl with rare-earth metal ions, the fluorescence maximum of F1 is blue shifted, the fluorescence lifetime is shortened, and the triplet-triplet (T-T) absorption spectrum of Fl disappears. This is because the lowest excited state is changed from the n,π* triplet state of Fl to the π,π* singlet states of Fl-rare-earth metal ion complexes by the complexation.

By the strong complex formation between Fl and rare-earth metal ions, electron transfer from electron donors (for instance, an alkylbenzene) is accelerated as compared to those of uncomplexed Fl, and the oxidizing ability of the excited state Fl is enhanced as indicated by the significant acceleration in the fluorescence quenching rates of Fl-rare earth metal ion complexes.

The one-electron reduction potential of the singlet excited state of the 1:2 complex formed between Fl and $Sc^{3+}$, i.e. $^1(Fl-2Sc^{3+})^*$ [* denotes the excited state, hereinafter referred to the same], is positively shifted by 780 mV as compared to $^1Fl^*$.

No photooxidation of p-chlorobenzyl alcohol by Fl occurs in deaerated MeCN. However, by enhancing the redox reactivity of $^1(Fl-2Sc^{3+})^*$ as compared to that of $^1Fl^*$, there can be efficiently oxidized p-chlorobenzyl alcohol to p-chlorobenzaldehyde by $^1(Fl-2Sc^{3+})^*$. The quantum yield for the photooxidation of p-chlorobenzyl alcohol by $Fl-2Sc^{3+}$ is the largest among various Fl-metal ion complexes.

The comparison of the reaction rate constant derived from the dependence of the quantum yield on the concentration of p-chlorobenzyl alcohol with the fluorescence quenching rate constant by electron transfer from the alcohol and the direct detection of radical intermediates reveal that the photooxidation proceeds via electron transfer from p-chlorobenzyl alcohol to $^1(Fl-2Sc^{3+})^*$.

Under an atmospheric pressure of oxygen, the photooxidation of p-methoxybenzyl alcohol by oxygen proceeds efficiently using $Fl-Lu^{3+}$ as a photocatalyst. Efficient photooxidation can be carried out in the case of $Fl-Lu^{3+}$, even with benzyl alcohol for which photocatalytic oxidation has been difficult in $Fl-Mg^{2+}$.

According to the study made by the present inventor, it has been found out that the riboflavin-2',3',4',5'-tetraacetate (Fl) forms not only 1:1 but also 1:2 complexes with rare-earth metal ions and that the Fl-rare-earth metal ion complexes are stable for the photodegradation and remarkably excellent in oxidizing ability with little deactivation of the catalytic activity, as compared to the Fl-divalent metal ion ($Mg^{2+}$) complex in the photocatalytic oxidation of benzyl alcohol derivatives by oxygen.

Remarkable enhancement in the redox reactivity of the photoexcited state of Fl-rare-earth metal ion complexes can be evaluated quantitatively by comparing and analyzing the relationship between the reaction rate constant for photoelectron transfer and its free energy with that of the $Fl-Mg^{2+}$ complex and the uncomplexed Fl.

The present inventor has found that a 1:2 complex formed between Fl and $Sc^{3+}$ ($Fl-2Sc^{3+}$) shows the largest reactivity among the Fl-metal ion complexes. The reaction mechanism for the photooxidation of benzyl alcohol derivatives by $Fl-2Sc^{3+}$ and the photocatalytic oxidation by oxygen is revealed based on the dependence of quantum yields on the alcohol concentration and the direct detection of the reactive intermediates in the photochemical reaction by the laser flash photolysis.

Next, the present invention will be described more specifically on the basis of each of Examples set forth below. However, the present invention is not intended to be limited only to each of Examples.

EXAMPLE 1

Raw Materials

A flavin analogue (riboflavin-2',3',4',5'-tetraacetate, Fl) was prepared by a reaction of riboflavin [manufactured by Wako Pure Chemicals Industries, Ltd.] with acetic anhydride in pyridine, and purified by recrystallization from ethanol-chloroform.

Benzene derivatives (toluene, ethylbenzene, m-xylene, o-xylene, p-cymene, p-xylene, 1,2,3-trimethylbenzene, 1,2,4-trimethylbenzene, 1,2,3,5-tetramethylbenzene, 1,2,3,4-tetramethylbenzene, pentamethylbenzene, and m-dimethoxybenzene) used as electron donors in fluorescence quenching experiments were obtained from Tokyo Kasei Kogyo Co., Ltd.

In addition, p-methoxybenzyl alcohol, p-chlorobenzyl alcohol, p-methoxybenzaldehyde, and p-chlorobenzaldehyde were obtained from Tokyo Kasei Kogyo Co., Ltd.

Potassium iron (III) trioxalate used as an actinometer was prepared, and purified by recrystallization from hot water.

Anhydrous magnesium perchlorate was obtained from Nacalai Tesque, Inc.

Scandium triflate $[Sc(OTf)_3]$ was prepared according to the following method. A deionized aqueous solution was mixed at a volume ratio of 1:1 with trifluoromethanesulfonic acid (>99.5%, 10.6 mL) obtained from Central Glass, Co., Ltd.

The above-mentioned trifluoromethanesulfonic acid solution was slowly added to a flask which contained scandium oxide ($Sc_2O_3$) (>99.9%, 30 mmol) obtained from Shin-Etsu Chemical, Co., Ltd. The resulting mixture was refluxed at 100° C. for 3 hours.

After the centrifugation of the reaction mixture, the solution containing scandium triflate was separated, and water was removed by vacuum distillation. Scandium triflate was dried under vacuum evacuation for 40 hours. Similarly, lutetium triflate and ytterbium triflate were prepared by the reaction of lutetium oxide and ytterbium oxide with an aqueous solution of trifluormethanesulfonic acid.

Lanthanum triflate was obtained from Aldrich as hexahydrate form, and used after drying under vacuum evacuation for 40 hours. Magnesium triflate $[Mg(OTf)_2]$ obtained from Aldrich was used as received.

1-Benzyl-1,4-dihydronicotinamide dimer $[(BNA)_2]$ was prepared, purified using acetonitrile as a solvent, and dried. Acetonitrile-$d_3$ and chloroform-d were obtained from EURI SO-TOP, CEA [France].

EXAMPLE 2

Reaction Procedures and Analysis

To an NMR tube that contained an acetonitrile-$d_3$ ($CD_3CN$) solution (0.6 mL) of p-$ClC_6H_4CH_2OH$ ($2.0\times10^{-2}$ M) was added Fl ($1.0\times10^{-2}$ M) in the presence of $Sc(OTf)_3$ ($3.0\times10^{-2}$ M) in an argon gas atmosphere.

The solution was deaerated by bubbling with argon gas for 5 minutes, and the NMR tube was sealed with a rubber septum.

The solution was irradiated with photo rays for 9 hours with a xenon lamp [manufactured by USHIO, INC. under the product number of UI-501C] through a Pyrex(registered trademark) filter transmitting photo rays having a wavelength of λ>420 nm.

The oxidation product of p-$ClC_6H_4CH_2OH$ was identified by comparing the $^1$H-NMR spectrum with that of a known compound.

The yield of the reaction product was determined based on the concentration of an internal standard, 1,4-dioxane ($2.0\times10^{-3}$ M).

$^1$H-NMR spectrum was measured with an NMR spectrometer manufactured by JAPAN ELECTRON OPTICS LABORATORY CO., LTD. (JEOL, Ltd.) under the trade name of JNM-GSX-400 (400 MHz) at a temperature of 300 K. The results are as follows.

$^1$H-NMR (CD$_3$CN, 298 K); δ (Me$_4$Si, ppm): p-ClC$_6$H$_4$CHO, δ 7.5 (m, 2H), 7.8 (m, 2H), 9.9 (s, 1H, CHO).

The photooxidation of p-MeOC$_6$H$_4$CH$_2$OH with Fl in the presence of Lu(OTf)$_3$ in oxygen-saturated MeCN was performed as follows.

p-MeOC$_6$H$_4$CH$_2$OH (3.0×10$^{-3}$ M) was added to the MeCN solution of Fl (2.0×10$^{-4}$ M) in the presence of Lu(OTf)$_3$ (1.0×10$^{-2}$ M) in a quartz cuvette (inner diameter: 10 mm).

The solution was purged with oxygen gas for 5 minutes and irradiated with the monochromatized light (λ=430 nm, slit width: 20 nm) from a SHIMADZU Spectrofluorophotometer (RF-5000) manufactured by Shimadzu Corporation.

The aliquot of the reaction solution was diluted and introduced into a SHIMADZU Gas Chromatography-Mass Spectrometer System (GC17A-QP5000) manufactured by Shimadzu Corporation to measure the amount of the oxidation reaction product, p-MeOC$_6$H$_4$CHO and the reactant, p-MeOC$_6$H$_4$CH$_2$OH.

The amount of reduction reaction product H$_2$O$_2$ was determined by the standard method (titration by iodide ion), and the diluted MeCN solution of a reaction product was treated with an excess amount of sodium iodide. The amount of I$_3^-$ formed was determined by the visible spectrum (λ$_{max}$=362 nm, ε=1.3×10$^4$ M$^{-1}$ cm$^{-1}$)with use of a Hewlett Packard 8452A Diode Array Spectrophotometer manufactured by Hewlett Packard.

EXAMPLE 3

Spectral Measurements

The formation of Fl-rare-earth ion complexes was examined from the change in the UV-Vis spectra of Fl (1.0×10$^{-4}$ M) in the presence of various concentrations of Yb(OTf)$_3$ (6.6×10$^{-5}$–2.7×10$^{-3}$ M), Lu(OTf)$_3$ (6.6×10$^{-5}$–2.7×10$^{-3}$ M), La(OTf)$_3$ (6.6×10$^{-5}$–2.8×10$^{-3}$ M), Mg(OTf)$_2$ (1.0×10$^{-4}$–5.0×10$^{-1}$ M) and Sc(OTf)$_3$ (6.5×10$^{-6}$–7.3×10$^{-4}$ M) with use of a Hewlett Packard 8452A Diode Array Spectrophotometer manufactured by Hewlett Packard.

The formation constants were obtained from the change in the UV-Vis spectra due to the formation of the 1:1 complexes, Fl-Yb$^{3+}$ (λ$_{max}$=376 and 430 nm), Fl-Lu$^{3+}$ (λ$_{max}$=362 and 438 nm), Fl-La$^{3+}$ (λ$_{max}$=370 and 434 nm), Fl-Mg$^{2+}$ (λ$_{max}$=360 and 436 nm), and the 1:2 complex, Fl-2Sc$^{3+}$ (λ$_{max}$=384 and λ$_{max}$=426 nm).

The measurements of IR spectra of rare-earth ion complexes with Fl (Fl-2Sc$^{3+}$, Fl-Yb$^{3+}$ and Fl-Mg$^{2+}$) in MeCN were performed on a SHIMADZU-FTIR8200PC Spectrophotometer manufactured by Shimadzu Corporation.

The quantum yields on the photochemical reaction of Fl with p-ClC$_6$H$_4$CH$_2$OH under a deaerated condition in the presence of Sc$^{3+}$ ion as well as the photooxidation of p-MeOC$_6$H$_4$CH$_2$OH by oxygen using Fl as a catalyst in the presence of Lu$^{3+}$ ion in MeCN were determined with a standard actinometer (potassium iron(III) trioxalate).

In the case of the photooxidation of p-ClC$_6$H$_4$CH$_2$OH with Fl, a square quartz cuvette (inner diameter: 10 mm) which contained a deaerated MeCN solution of Fl (1.0×10$^{-2}$ M) and p-ClC$_6$H$_4$CH$_2$OH (1.0×10$^{-2}$–8.0×10$^{-1}$ M) in the presence of Sc(OTf)$_3$ (1.0×10$^{-2}$ M) was irradiated with the monochromatized light (λ=430 nm) having a slit width of 20 nm from a SHIMADZU Spectrofluorophotometer (RF-5000) manufactured by Shimadzu Corporation.

The light intensity of monochromatized light of λ=430 nm was determined as 4.7×10$^{-8}$ einstein•dm$^{-3}$ s$^{-1}$ with a slit width of 20 nm. The photochemical reaction was monitored by a Hewlett Packard 8452A Diode Array Spectrophotometer manufactured by Hewlett Packard.

The quantum yields under deaerated conditions were determined from the decrease in absorption due to Fl at λ$_{max}$=430 nm in MeCN. The quantum yields for the photooxidation of p-MeOC$_6$H$_4$CH$_2$OH by oxygen in the presence of Lu$^{3+}$ in MeCN were determined from the increase in absorbance at λ=350 nm due to the reaction product p-MeOC$_6$H$_4$CHO which was identified by the GC-MS analysis.

EXAMPLE 4

Fluorescence Quenching Experiments

Fluorescence quenching experiments of Fl-metal ion complexes were carried out with a SHIMADZU Spectrophotometer (RF-5000) manufactured by Shimadzu Corporation.

The excitation wavelength of Fl and Fl-metal ion complexes (Fl-2Sc$^{3+}$, Fl-Yb$^{3+}$ and Fl-Mg$^{2+}$) was 460 nm in deaerated and aerated MeCN.

The monitoring wavelengths correspond to the maxima of the emission wavelengths at λ$_{max}$=486 nm (Fl-2Sc$^{3+}$), λ$_{max}$=500 nm (Fl-Yb$^{3+}$), λ$_{max}$=504 nm (Fl-Mg$^{2+}$) and λ$_{max}$=506 nm (Fl).

The MeCN solutions were deaerated by argon purging for 7 minutes prior to the measurements. Relative fluorescence intensities were measured for MeCN solutions containing Fl (1.0×10$^{-5}$ M) with various alkylbenzenes (1.0×10$^{-2}$–9.6×10$^{-1}$ M) in the presence or absence of metal ions (1.0×10$^{-2}$ M). Although there was no change in the shape, there was a change in the intensity of the fluorescence spectrum by the addition of a quencher. This change is expressed by the Stern-Volmer relationship represented by the equation (1):

$$I_0/I = 1 + K_q[D] \qquad (1)$$

wherein [D] is a concentration of the donor used as a quencher, I$_0$ is fluorescence intensity when there is no quencher, and I is fluorescence intensity when the quencher exists.

The fluorescence lifetimes (τ) of the metal ion complexes of Fl were determined in deaerated MeCN containing metal ions at a temperature of 298 K with a HORIBA NAES-1100 Time-Resolved Spectrofluorophotometer manufactured by HORIBA, Ltd.

EXAMPLE 5

Laser Flash Photolysis

Triplet-triplet transient absorption spectra of Fl and a complex formed between Fl-Yb$^{3+}$ were measured by laser flash photolysis of an MeCN solution containing Fl (1.0×10$^{-5}$ M) in the presence or absence of Yb(OTf)$_3$ (1.0×10$^{-2}$ M). For the detection of the transient absorption spectra in the photochemical reaction of the Fl-Sc(OTf)$_3$ complex with p-ClC$_6$H$_4$CH$_2$OH, a deaerated MeCN solution containing Fl (1.0×10$^{-4}$ M), p-ClC$_6$H$_4$CH$_2$OH (1.0 M), and Sc(OTf)$_3$ (1.0×10$^{-2}$ M) was excited at 440 nm with an Nd:YAG laser (Continuum, Surelite II-10) with the power of 10 mJ.

The transient spectra were determined using fresh solutions in each laser excitation. All of the experiments were performed at a temperature of 298 K.

EXAMPLE 6

Electrochemical Measurement

Redox potentials of various benzene derivatives ($2.0 \times 10^{-3}$ M) in MeCN containing 0.10 M TBAP [tetrabutylammonium perchlorate] as a supporting electrolyte were determined at room temperature by SHACV (second harmonic ac voltammetry) method under deaerated conditions using a three-electrode system and a 100B electrochemical analyzer manufactured by BAS.

The working and counter electrodes were platinum, while $Ag/AgNO_3$ (0.01M) was used as a reference electrode. All of the potentials (against $Ag/Ag^+$) were converted to values for SCE by adding 0.29 V.

EXAMPLE 7

ESR Measurements

Fl was dissolved in MeCN (3.3 mg; $6.0 \times 10^{-3}$ M in 10 mL), and purged with argon for 10 minutes. $Sc(OTf)_3$ (9.8 mg; $2.0 \times 10^{-2}$ M in 1.0 mL) was also dissolved in deaerated MeCN.

The Fl solution (200 µL) and $Sc(OTf)_3$ solution (200 µL) were introduced into the ESR cell (inner diameter: 0.8 mm) containing $(BNA)_2$ (1.0 mg), and stirred with bubbling with argon gas through a syringe with a long needle.

The ESR spectra of $Fl^{\bullet -}$-$2Sc^{3+}$ were recorded on a JEOL JES-RE1XE spectrometer, with irradiation of a high-pressure mercury lamp (USH-1005D) focusing at the sample cell in the ESR cavity at a temperature of 298 K.

The ESR spectra of $Fl^{\bullet -}$ were also determined in the absence of $Sc(OTf)_3$ under otherwise the same experimental conditions. The modulation of the magnetic field was determined by selecting a signal-to-noise (S/N) ratio of the spectra to be a maximum under nonsaturating microwave power conditions.

EXAMPLE 8

Theoretical Values

Density functional calculation was performed on a COMPAQ DS20E computer using B3LYP for the open shell molecule. B3LYP optimized structures for N(10)-methyl flavin radical anion were determined using the 6-311++G ground state and the Gaussian 98 program. The $<S^2>$ value was determined as 0.763, indicating that there is no problem in the doublet state.

[Results and Discussion]

1. Complex Formed Between Fl and Metal Ions

The UV-Vis absorption spectra of Fl in MeCN are significantly affected by the addition of metal ions. The absorption band of Fl at 362 nm is red shifted and the absorption band of Fl at 438 nm is blue shifted in the presence of metal ions. As shown in FIG. 1 regarding the Fl-$Sc^{3+}$ complex, isosbestic points are observed at 300 nm, 354 nm and 425 nm at low concentrations of $Sc(OTf)_3$.

However, the isosbestic points observed at the low $Sc(OTf)_3$ concentrations are spread over slightly when the $Sc(OTf)_3$ concentration increases, and new isosbestic points are observed at 302 nm, 362 nm and 467 nm at a higher $Sc(OTf)_3$ concentration.

Such spectroscopic changes may be interpreted to be based on the formation of complexes between Fl and $Sc(OTf)_3$ via two steps.

In a first step, a 1:1 complex is formed as represented by the equation (2):

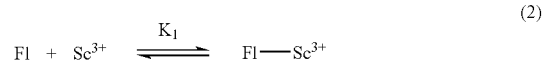

(2)

and in a second step, a 1:2 complex is formed as represented by the equation (3):

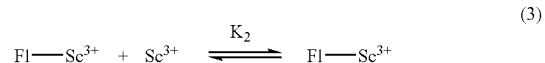

(3)

by the coordination of $Sc^{3+}$ to Fl. Similar two-step spectroscopic changes are also observed when $Sc(OTf)_3$ is replaced by $La(OTf)_3$ or $Mg(ClO_4)_2$.

The equilibrium constant ($K_1$) in the equation (2) is obtained by the equation (4):

$$(\alpha^{-1}-1)^{-1} = K_1([Sc^{3+}]_0 - [Fl]_0) \qquad (4)$$

wherein $[Sc^{3+}]_0$ and $[Fl]_0$ are initial concentrations, and $\alpha = (A-A_0)/(A_f-A_0)$ A is absorbance at 384 nm in the presence of $Sc(OTf)_3$, $A_0$ and $A_f$ are initial and final absorbances at the same wavelength in the presence or in the absence of an excess of $Sc(OTf)_3$ such that all the Fl molecules form the 1:1 complex (Fl-$Sc^{3+}$), respectively.

Figure 2:
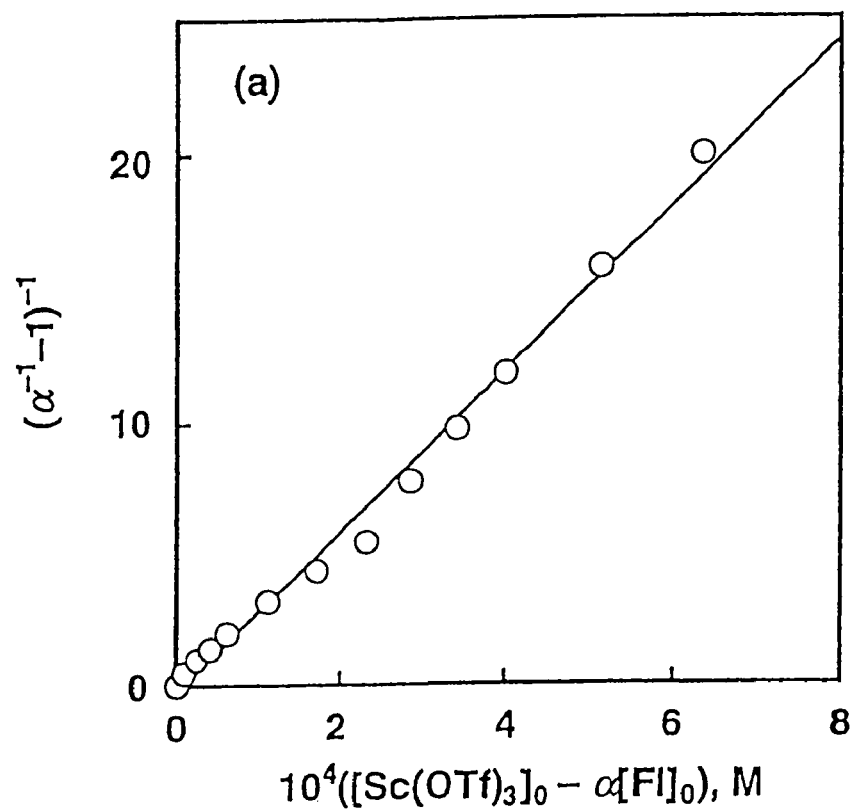
FIG. 2 is a graph showing determination results for the complex formation constants $K_1$, and $K_2$ for the complex formation of Fl ($1.0 \times 10^{-4}$ M) with $Sc^{3+}$ in MeCN.
Figure 2:
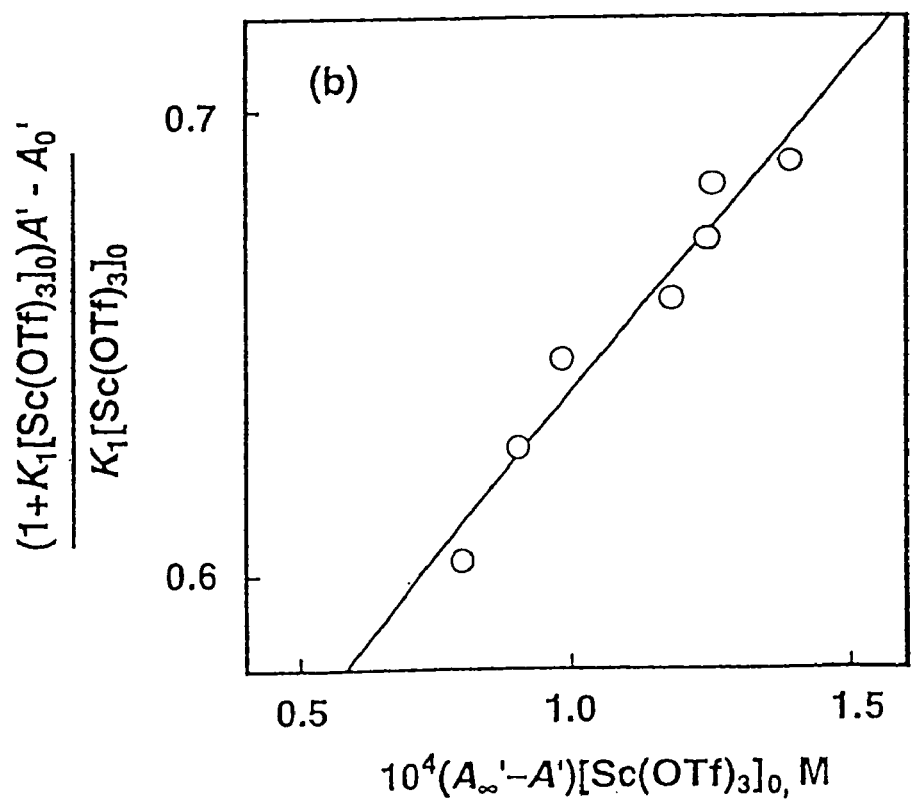

The linear plot between $(\alpha^{-1}-1)^{-1}$ and $([Sc^{3+}]_0-[Fl]_0)$ is shown in FIG. 2(a). The $K_1$ value is determined from the slope of the linear plot in FIG. 2(a).

The $K_2$ value in the equation (3) is obtained using $K_1$ value as follows. The absorbance $A^1$ at 452 nm due to the Fl-$2SC^{3+}$ complex is expressed by the equation (5):

$$[(1+K_1[Sc^{3+}]_0 A^1 - A_0^1]/K_1[Sc^{3+}]_0 = K_2(A_f^1 - A^1)[Sc^{3+}]_0 + A^1 \qquad (5)$$

wherein each of $A_0$ and $A^1$ is absorbance at 452 nm due to Fl in the absence of $Sc(OTf)_3$ and absorbance at 452 nm due to $F^1$-$SC^{3+}$ in the presence of $Sc(OTf)_3$, and $A_f^1$ is the absorbance due to Fl-$2Sc^{3+}$ in the presence of a large excess of $Sc(OTf)_3$ such that all Fl molecules form the 1:2 complex (Fl-$2Sc^{3+}$) with $Sc(OTf)_3$.

In the equation (5), the value of the left-hand side is obtained using the $K_1$ value, and the $K_2$ value can be determined from the slope of a linear plot between the left-hand side in the equation (5) and $(A_f^1-A^1)[Sc^{3+}]_0$. The linear plot as described above is as shown in FIG. 2(b), which is in agreement with the equation (5).

The $K_1$ and $K_2$ values obtained for the Fl-metal ion complexes are listed in Table 1.

TABLE 1

| | $Mg^{2+}$ | $Lu^{3+}$ | $Yb^{3+}$ | $La^{3+}$ | $Sc^{3+}$ |
|---|---|---|---|---|---|
| $K_1$, $M^{-1}$ | $2.2 \times 10^2$ | $4.1 \times 10^2$ | $8.8 \times 10^2$ | $4.5 \times 10^3$ | $3.1 \times 10^4$ |
| $K_2$, $M^{-1}$ | 0.6 | — | — | $1.6 \times 10^2$ | $1.4 \times 10^3$ |

The $K_1$ value increases in the order of $Mg^{2+} < Lu^{3+} < Yb^{3+} < La^{3+} < Sc^{3+}$. The $K_2$ value increases in the same order, although the $K_2$ values of the 1:2 complexes of Fl with $Yb^{3+}$ or $Lu^{3+}$ could not be determined because of the low solubility of $Yb(OTf)_3$ and $Lu(OTf)_3$ in MeCN.

IR spectra of Fl in MeCN show three C=O stretching bands assignable to the $C^2$- and $C^4$-, and acetate carbonyl groups.

When an excess amount of a metal ion such that most Fl molecules form the metal ion complex is added to the MeCN solution of Fl, all the C=O stretching bands are significantly red shifted as listed in Table 2.

TABLE 2

| | $\nu(C^2 = O)$, $cm^{-1}$ | $\nu(C^4 = O)$, $cm^{-1}$ |
|---|---|---|
| none[a] | 1689 | 1718 |
| $[Mg^{2+}]$[b] | 1645 | 1650 |
| $[Yb^{3+}]$[c] | 1620 | 1699 |
| $[Sc^{3+}]$[d] | 1606 | 1677 |

[a]In the absence of metal ions.
[b]$1.0 \times 10^{-1}$ M.
[c]$1.0 \times 10^{-2}$ M.
[d]$3.0 \times 10^{-2}$ M.

Especially, the C=O stretching band due to the $C^2$-carbonyl group of Fl-$2Sc^{3+}$ are largely red shifted by about 80 $cm^{-1}$, which suggests that interaction with $C^2$-carbonyl group is stronger than that with $C^4$-carbonyl group.

2. Fluorescence Quenching of Fl-Metal Ion Complexes

By the complexation of Fl with metal ions, the maxima of the fluorescence emission wavelength are blue shifted, and the fluorescence lifetime is shortened.

The maxima of the fluorescence emission wavelength and the lifetime of the singlet excited state of Fl in the presence and in the absence of metal ions (0.01 M) were determined. The results are as listed in Table 3.

TABLE 3

| metal ion[a] | $\lambda_{max}$, nm | $\tau$, ns | $E^0_{red}{}^*$, V vs SCE | $\Delta G^o{}_0$, kcal $mol^{-1}$ |
|---|---|---|---|---|
| none | 506 | 6.5 | 1.67 | 3.4 |
| $Mg^{2+}$ | 504 | 1.3 | 2.06 | 4.0 |
| $Yb^{3+}$ | 500 | 0.9 | 2.25 | 4.5 |
| $Sc^{3+}$ | 486 | 2.4 | 2.45 | 4.7 | none: In the absence of metal ions.
[a]0.01 M.

In the case of $Sc^{3+}$, the largest blue shift is observed when Fl forms a 1:2 complex (Fl-$2Sc^{3+}$) with 0.01 M $Sc^{3+}$ (Table 2).

The complexation of Fl with metal ions also results in the change in the lowest excited state from the n,$\pi^*$ triplet state to the $\pi,\pi^*$ singlet state, as indicated by the disappearance of the triplet-triplet (T-T) absorption spectrum of Fl by the complexation with $Yb^{3+}$.

Figure 3:
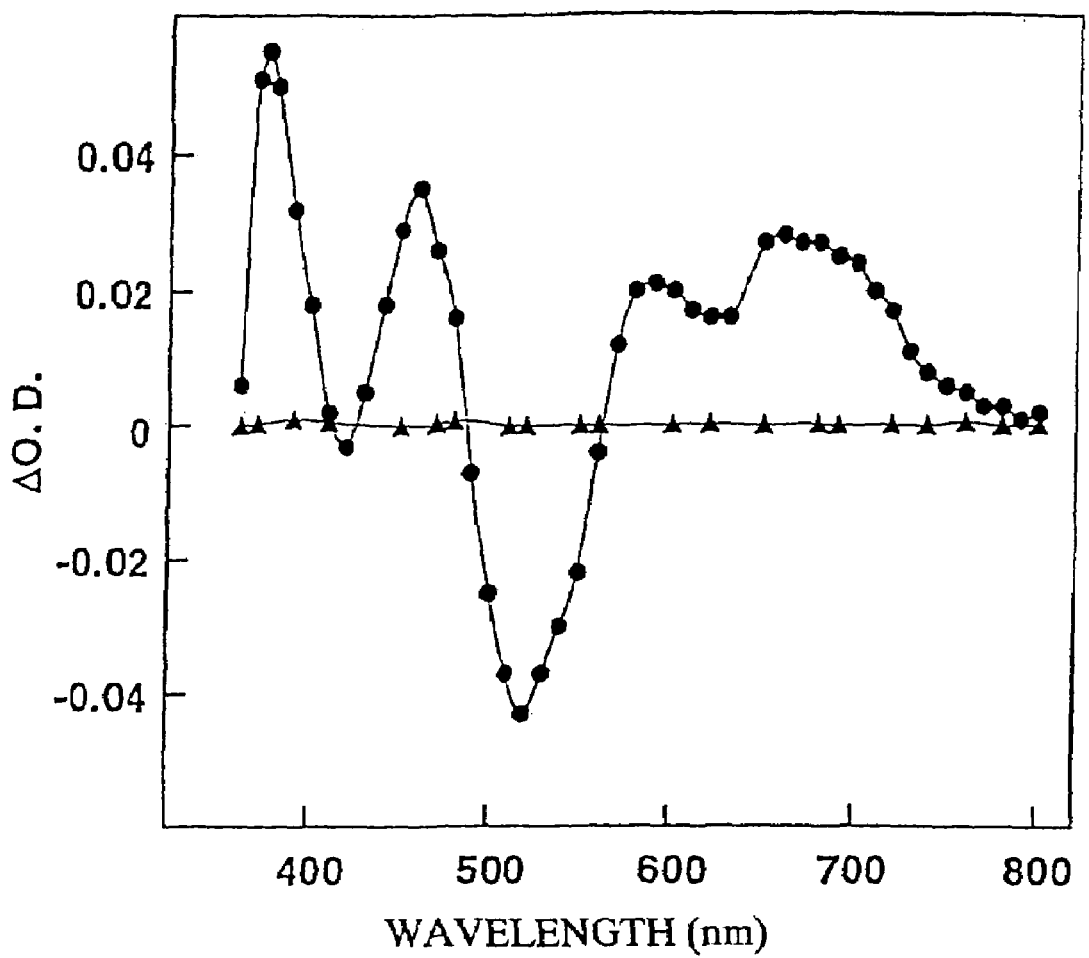
FIG. 3 is a transient absorption spectrum obtained by laser flash photolysis of Fl ($1.0 \times 10^{-5}$ M) in the absence (symbol: ○) and presence of $Yb^{3+}$ (symbol: Δ, $1.0 \times 10^{-2}$ M) in deaerated MeCN at 3.0 μs after laser excitation at 355 nm.

The T-T absorption spectrum of Fl in MeCN shown in FIG. 3 shows absorption maxima at $\lambda$=395, 475, 585 and 655 nm which agree with the literature values in the absence of metal ions.

The T-T absorption spectrum diminishes completely in the presence of $Yb(OTf)_3$ (0.01 M) under otherwise the same experimental conditions.

The change in the lowest excited state may be caused by the complexation of Fl with the metal ion. The nonbonding orbital is more stabilized than the $\pi$-orbital due to a stronger interaction between non-bonding electrons and the metal ion.

On the other hand, the $\pi$-$\pi^*$ singlet excited state is more stabilized by the interaction with the metal ion, that is singlet, than the $\pi$-$\pi^*$ triplet excited state. Therefore, the $\pi$-$\pi^*$ singlet excited state becomes the lowest excited state in the Fl-metal ion complex as compared with the lowest n,$\pi^*$ triplet excited state in the uncomplexed Fl.

The change in the lowest excited state from the n-$\pi^*$ triplet excited state to the $\pi$-$\pi^*$ singlet excited state has also been observed when aromatic carbonyl compounds form the complexes with $Mg^{2+}$ ion.

The fluorescence of Fl is quenched via photoinduced electron transfer from electron donors to the singlet excited state ($^1Fl^*$) in MeCN. The effects of metal ions on the oxidizing ability of the singlet excited state of Fl are examined by comparing the quenching rate constants ($k_q$) in the presence of a metal ion with those in its absence.

The fluorescence of (Fl-$2Sc^{3+}$)* is efficiently quenched by a relatively weak electron donor such as toluene as represented by the equation (6):

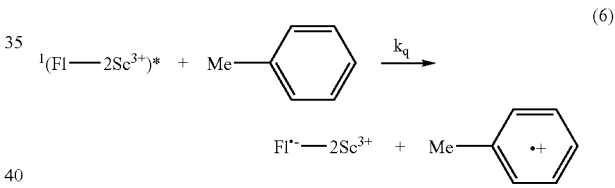

(6)

No fluorescence quenching by toluene occurred in the case of the Fl-$Mg^{2+}$ complex or Fl in the absence of the metal ion.

From the slope of the Stern-Volmer plots [equation (1)], there were obtained quenching constants $K_q$(=$k_q\tau$,$\tau$=the fluorescence lifetime) for the fluorescence quenching of Fl by alkyl-substituted or methoxy-substituted benzenes in the presence and in the absence of $Sc(OTf)_3$, $Yb(OTf)_3$ and $Mg(ClO_4)_2$.

The $k_q$ values are listed in Table 4 together with the one-electron oxidation potentials ($E^0_{ox}$) of the electron donors.

TABLE 4

| | | $E^0_{ox}$, [a]V | $k_q$, $M^{-1}$ $s^{-1}$ | | | |
|---|---|---|---|---|---|---|
| No. | Substituted Benzene | vs SCE | $Sc^{3+}$ | $Yb^{3+}$ | $Mg^{2+}$ | none[b] |
| 1 | Toluene | 2.20 | $1.0 \times 10^9$ | $1.3 \times 10^8$ | c | c |
| 2 | Ethylbenzene | 2.14 | $1.5 \times 10^9$ | $3.8 \times 10^8$ | c | c |
| 3 | m-Xylene | 2.02 | $3.8 \times 10^9$ | — | $6.3 \times 10^8$ | c |
| 4 | o-Xylene | 1.98 | $4.8 \times 10^9$ | $1.9 \times 10^9$ | $7.0 \times 10^8$ | c |
| 5 | p-Cymene | 1.96 | $4.4 \times 10^9$ | — | $1.3 \times 10^9$ | c |
| 6 | p-Xylene | 1.93 | $5.7 \times 10^9$ | $2.6 \times 10^9$ | $1.4 \times 10^9$ | c |
| 7 | 1,2,3-Trimethylbenzene | 1.88 | $5.5 \times 10^9$ | $2.8 \times 10^9$ | $1.8 \times 10^9$ | c |

TABLE 4-continued

| No. | Substituted Benzene | $E^0_{ox}$,[a] V vs SCE | $k_q$, $M^{-1}$ $s^{-1}$ | | | |
|---|---|---|---|---|---|---|
| | | | $Sc^{3+}$ | $Yb^{3+}$ | $Mg^{2+}$ | none[b] |
| 8 | 1,2,4-Trimethylbenzene | 1.79 | $6.5 \times 10^9$ | $4.1 \times 10^9$ | $2.3 \times 10^9$ | c |
| 9 | 1,2,3,5-Tetramethylbenzene | 1.71 | $7.6 \times 10^9$ | — | $4.2 \times 10^9$ | $1.2 \times 10^8$ |
| 10 | 1,2,3,4-Tetramethylbenzene | 1.71 | $7.8 \times 10^9$ | $6.4 \times 10^9$ | — | $1.5 \times 10^8$ |
| 11 | Pentamethylbenzene | 1.58 | — | $9.3 \times 10^9$ | $1.3 \times 10^{10}$ | $1.3 \times 10^9$ |
| 12 | m-Dimethyoxybenzene | 1.50 | $1.1 \times 10^{10}$ | — | — | $3.2 \times 10^9$ |

[a]Determined according to the SHACV method in MeCN containing 0.1 M TBAP.
[b]In the absence of metal ion.
[c]Too small to be determined accurately.

Figure 4:
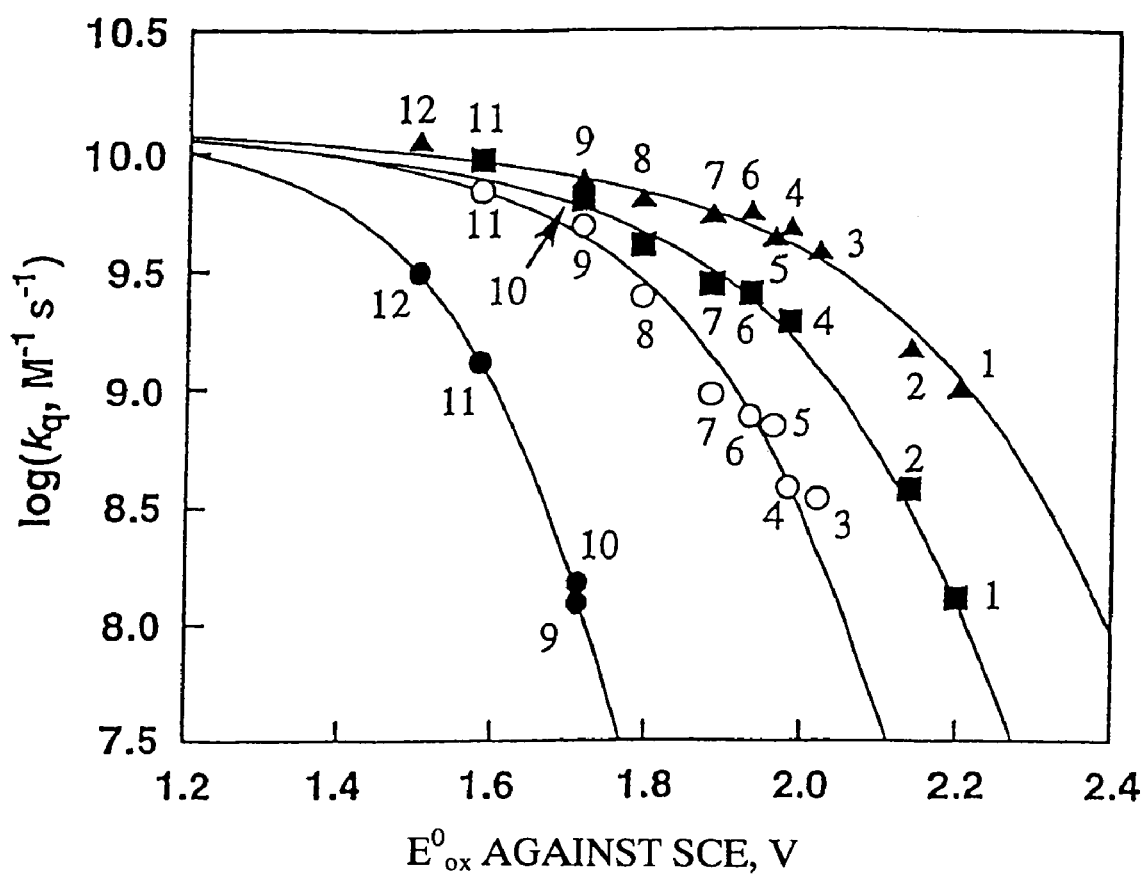
FIG. 4 is a graph of the quenching rate constant ($k_q$) for the fluorescence quenching of Fl in the presence of $Sc^{3+}$ (symbol: Δ), $Yb^{3+}$ (symbol: □) and $Mg^{2+}$ (symbol: open ○) and the absence thereof (symbol: solid ○).

The quenching rate constants ($k_q$) increase with the decrease in the one-electron oxidation potentials of the electron donors to reach a diffusion limiting value as shown in FIG. 4. It can be seen from the above that the fluorescence quenching occurs by photoinduced electron transfer from electron donors to the singlet excited states of Fl-metal ion complexes.

The one-electron reduction potential ($E^0_{red}$* for SCE) of the singlet excited state of the Fl-metal ion complex can be determined by adaptation of the free energy relationship for photoinduced electron transfer from a series of electron donors to the singlet excited state of the Fl-metal ion complex in the presence of a metal ion ($1.0 \times 10^{-2}$ M) in MeCN at 298 K.

The free energy change ($\Delta G^0_{et}$) of photoinduced electron transfer from electron donors to the singlet excited state of the Fl-metal ion complex is obtained by the equation (7):

$$\Delta G^0_{et} = e(E^0_{ox} - E^0_{red}*) \tag{7}$$

wherein e is an electric charge, and $E^0_{ox}$ is a one-electron oxidation potential of an electron donor.

The dependence of the activation free energy of photoinduced electron transfer ($\Delta G^{\neq}_{et}$) on the free energy change ($\Delta G^0_{et}$) of electron transfer is expressed by the equation (8):

$$\Delta G^{\neq}_{et} = (\Delta G^0_{et}/2) + [(\Delta G^0_{et}/2)^2 + (\Delta G^{\neq}_0)^2]^{1/2} \tag{8}$$

wherein $\Delta G^{\neq}_0$ is a $\Delta G^{\neq}_{et}$ when the driving force of ● electron transfer is zero (0), i.e., $\Delta G^0_{et} = 0$.

On the other hand, the $\Delta G^{\neq}_{et}$ values are obtained from $k_q$ according to the equation (9):

$$\Delta G^{\neq}_{et} = 2.3 k_B T \log[Z(k_q^{-1} - k_{diff}^{-1})] \tag{9}$$

wherein $k_B$ is the Boltzmann constant, Z is a frequency factor that takes the value of $1 \times 10^{11}$ $M^{-1}s^{-1}$, and $k_{diff}$ is a diffusion rate constant ($2.0 \times 10^{10}$ $M^{-1}s^{-1}$) in MeCN.

From the equations (7) and (8), a linear relationship between $E^0_{ox} - (\Delta G^{\neq}_{et}/e)$ and $(e/\Delta G^{\neq}_{et})$ is derived, as represented by the equation (10):

$$E^0_{ox} - (\Delta G^{\neq}_{et}/e) = E^0_{red}* - (\Delta G^{\neq}_{et}/e)^2/(\Delta G^{\neq}_{et}/e) \tag{10}$$

Figure 5:
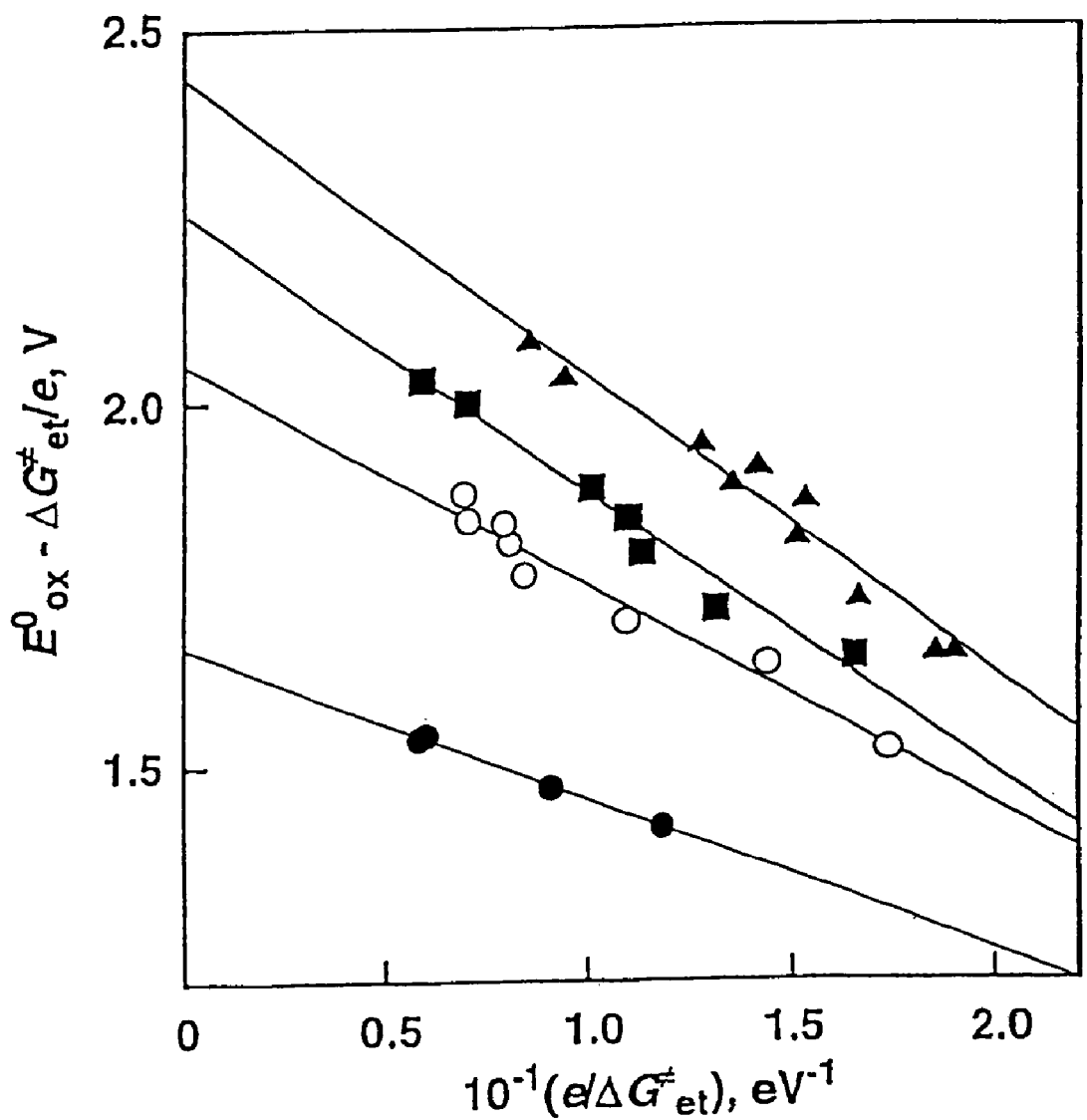
FIG. 5 is a graph showing the relationship between $E^0_{ox}-(\Delta G^{\neq}_{et}/e)$ and $(e/\Delta G^{\neq}_{et})$ for the data in FIG. 4.

The $\Delta G^{\neq}_{et}$ values are obtained from the $k_q$ values using the equation (9). As described above, the unknown values of $E^0_{red}*$ and $\Delta G^{\neq}_0$ can be determined from the intercept and slope of the linear plots of $E^0_{ox} - (\Delta G^{\neq}_{et}/e)$ against $(e/\Delta G^{\neq}_{et})$ as shown in FIG. 5.

The order of $E^0_{red}*$ (for SCE) values of the Fl-metal ion complexes is $^1(Fl-2Sc^{3+})*$ (2.45 V) > $^1(Fl-Yb^{3+})*$ (2.25 V) > $^1(Fl-Mg^{2+})*$ (2.06 V) > $^1Fl*$ (1.67 V), and this order is consistent with that of the formation constants ($K_1$) of Fl-metal ion complexes.

It can be seen from the comparison of the $E^0_{red}*$ value of $^1Fl-2Sc^{3+})*$ with that of $^1Fl*$, the $E^0_{red}*$ value of $^1(Fl-2Sc^{3+})*$ is remarkably shifted in the positive direction (about 780 mV) as compared with the $E^0_{red}*$ value of $^1Fl*$. By largely shifting the $E^0_{red}*$ value in a positive direction as described above, the reactivity of $^1(Fl-2Sc^{3+})*$ for uncomplexed Fl in the photoinduced electron transfer reactions is remarkably increased as shown in FIG. 4.

3. Photooxidation of p-Chlorobenzyl Alcohol by Fl-2Sc$^{3+}$

By remarkably enhancing the redox reactivity of $^1(Fl-2Sc^{3+})*$ as compared to that of the $^1(Fl-Sc^{3+})*$, p-chlorobenzyl alcohol can be oxidized efficiently by $^1(Fl-2Sc^{3+})*$.

Irradiation of a deaerated MeCN solution containing Fl, p-chlorobenzyl alcohol and Sc(OTf)$_3$ with visible light at λ>420 nm results in the formation of p-chlorobenzaldehyde and FlH$_2$ as represented by the equation (11):

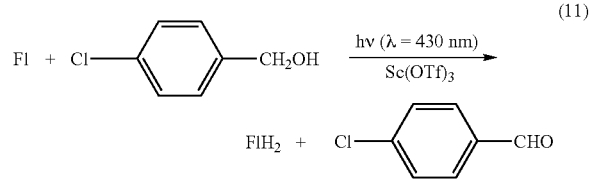

(11)

No photooxidation of p-chlorobenzyl alcohol occurred in the absence of the metal ion.

Similarly, the photooxidation of p-chlorobenzyl alcohol by Fl proceeded in the presence of other metal triflates such as La(OTf)$_3$, Lu(OTf)$_3$, Sc(OTf)$_3$ and Mg(OTf)$_2$.

The quantum yields for the photooxidation of p-chlorobenzyl alcohol ($8.0 \times 10^{-1}$ M) in the presence of Fl ($2.0 \times 10^{-4}$ M) and metal triflates were determined from the rate of disappearance of the absorption band due to the Fl-metal ion complexes under the irradiation of monochromatized light of λ=430 nm.

In the presence of $1.0 \times 10^{-2}$ M metal ion, Fl forms a 1:2 complex with Sc$^{3+}$ and La$^{3+}$, and a 1:1 complex with other metal ions (Table 1). The Φ values [quantum yields] are listed in Table 5.

The Φ value is largest in the case of Sc(OTf)$_3$ (Φ=0.17) and decreases in the order of Sc$^{3+}$>La$^{3+}$>Lu$^{3+}$>Yb$^{3+}$>Mg$^{2+}$.

When p-chlorobenzyl alcohol is replaced by p-methoxybenzyl alcohol that is a stronger electron donor, the Φ values of Fl-metal ion complexes become larger except for the case of Sc(OTf)$_3$ as shown in Table 5.

TABLE 5

| Metal Ion[a] | $\Phi(p\text{-}ClC_6H_4CH_2OH)$[b] | $\Phi(p\text{-}MeOC_6H_4CH_2OH)$[c] |
|---|---|---|
| $Sc^{3+}$ | $1.7 \times 10^{-1}$ | $1.2 \times 10^{-1}$ |
| $La^{3+}$ | $2.4 \times 10^{-2}$ | $5.7 \times 10^{-2}$ |
| $Lu^{3+}$ | $6.2 \times 10^{-3}$ | $1.7 \times 10^{-1}$ |
| $Yb^{3+}$ | $3.3 \times 10^{-3}$ | $6.0 \times 10^{-3}$ |
| $Mg^{2+}$ | $1.9 \times 10^{-3}$ | $6.6 \times 10^{-2}$ |

[a]Metal ion being used as a triflate salt: [metal ion] = $1.0 \times 10^{-2}$ M.
[b][Fl] = $2.0 \times 10^{-4}$ M, [p-ClC$_6$H$_4$CH$_2$OH] = $8.0 \times 10^{-1}$ M.
[c][Fl] = $3.0 \times 10^{-4}$ M, [p-MeOC$_6$H$_4$CH$_2$OH] = $2.7 \times 10^{-2}$ M.

Figure 6:
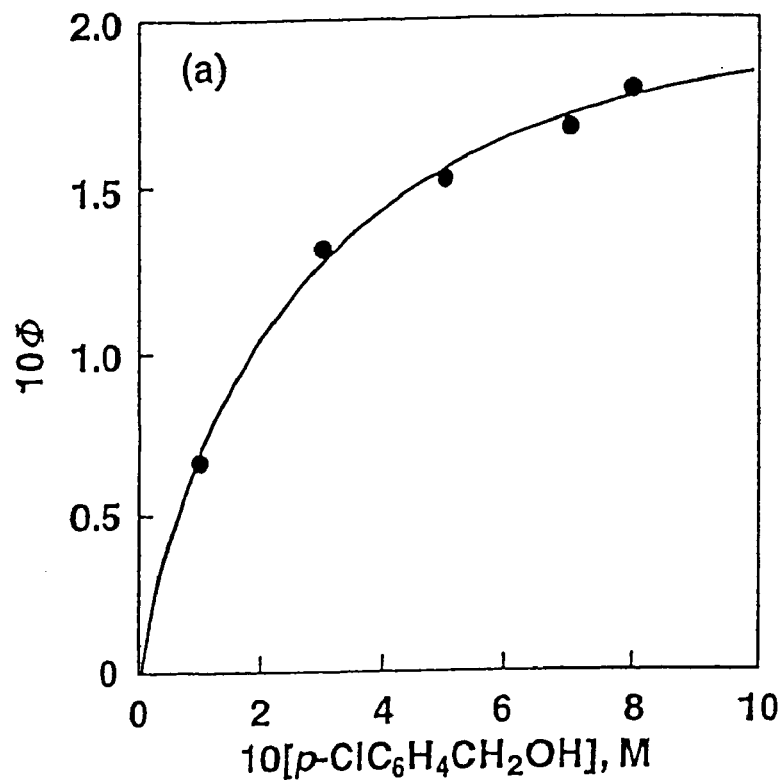
FIG. 6(a) is a graph showing the relationship between a concentration of [p-ClC$_6$H$_4$CH$_2$OH] and a quantum yield (Φ)
FIG. 6(b) is a graph showing the relationship between $\Phi^{-1}$ and [p-ClC$_6$H$_4$CH$_2$OH]$^{-1}$.
Figure 6:
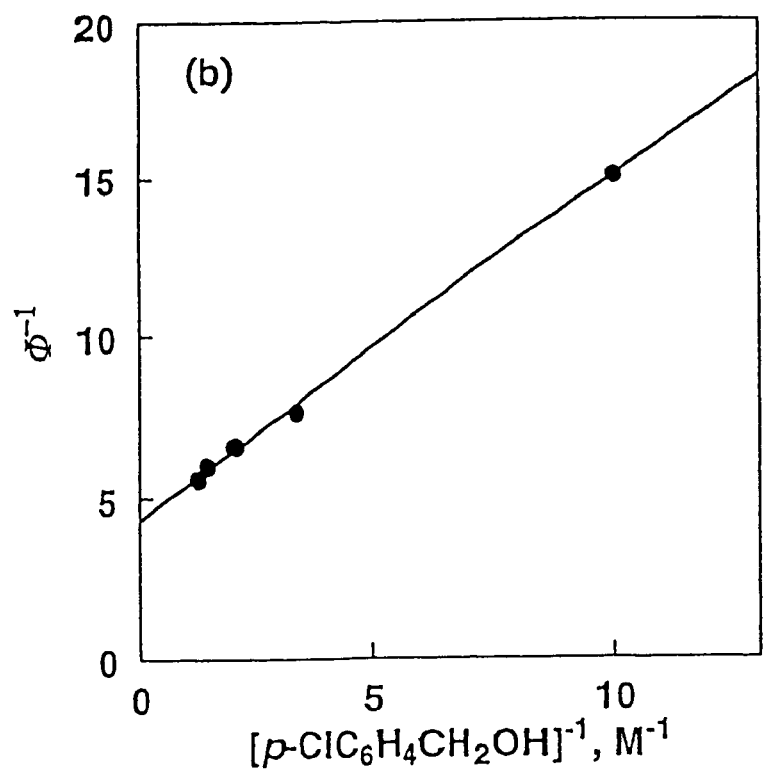

The $\Phi$ value for the photooxidation of p-chlorobenzyl alcohol [p-ClC$_6$H$_4$CH$_2$OH] to p-chlorobenzaldehyde in MeCN increases with an increase in the concentration of p-chlorobenzyl alcohol to approach a limiting value ($\Phi_\infty$) as shown in FIG. 6(a).

The dependence of the quantum yields on [p-ClC$_6$H$_4$CH$_2$OH] is expressed by the equation (12):

$$\Phi = \Phi_\infty K_{obs}[p\text{-}ClC_6H_4CH_2OH] \div (1+K_{obs}[p\text{-}ClC_6H_4CH_2OH]) \quad (12)$$

wherein $K_{obs}$ is the quenching constant of $^1(Fl\text{-}2Sc^{3+})^*$ by p-ClC$_6$H$_4$CH$_2$OH.

The equation (12) can be expressed as a linear relationship between $\Phi^{-1}$ and [p-ClC$_6$H$_4$CH$_2$OH]$^{-1}$, as represented by the equation (13):

$$\Phi^{-1} = \Phi_\infty^{-1}[1+(K_{obs}[p\text{-}ClC_6H_4CH_2OH])^{-1}] \quad (13)$$

The establishment of the equation (13) can be confirmed by plotting $\Phi^{-1}$ for [p-ClC$_6$H$_4$CH$_2$OH]$^{-1}$ as shown in FIG. 6(b). From the slope and the intercept, the values of $\Phi_\infty$ ($2.3 \times 10^{-1}$) and $K_{obs}$ (4.0 M$^{-1}$) are obtained.

The quenching constant $K_{obs}$ (=$k_{obs}\tau$) is converted to a rate constant ($k_{obs}$=$1.6 \times 10^9$ M$^{-1}$ s$^{-1}$) of the reaction of $^1(Fl\text{-}2Sc^{3+})^*$ with p-chlorobenzyl alcohol using the fluorescence lifetime (2.4 ns).

Since the one-electron oxidation potential of p-chlorobenzyl alcohol ($E^0_{ox}$=1.88 V for SCE in MeCN) lies within the range of the oxidation potentials of substituted benzenes used for the fluorescence quenching of $^1(Fl\text{-}2Sc^{3+})^*$ via photoinduced electron transfer (Table 4), the fluorescence quenching of $^1(Fl\text{-}2Sc^{3+})^*$ by p-chlorobenzyl alcohol also occurred efficiently. The fluorescence quenching rate constant ($k_q$) of $^1(Fl\text{-}2Sc^{3+})^*$ by p-chlorobenzyl alcohol was obtained from the Stern-Volmer relationship (vide supra).

The $k_q$ value thus obtained is $1.8 \times 10^9$ M$^{-1}$ s$^{-1}$ which agrees with the $k_{obs}$ value. The agreement shows that the photooxidation of p-chlorobenzyl alcohol by Fl in the presence of Sc(OTf)$_3$ proceeds via electron transfer from p-chlorobenzyl alcohol to $^1(Fl\text{-}2Sc^{3+})^*$ which has much stronger oxidizing ability than $^1Fl^*$.

The occurrence of photoinduced electron transfer in the photooxidation of p-chlorobenzyl alcohol by Fl-2Sc$^{3+}$ has been confirmed by the laser flash photolysis study as follows.

Figure 7:
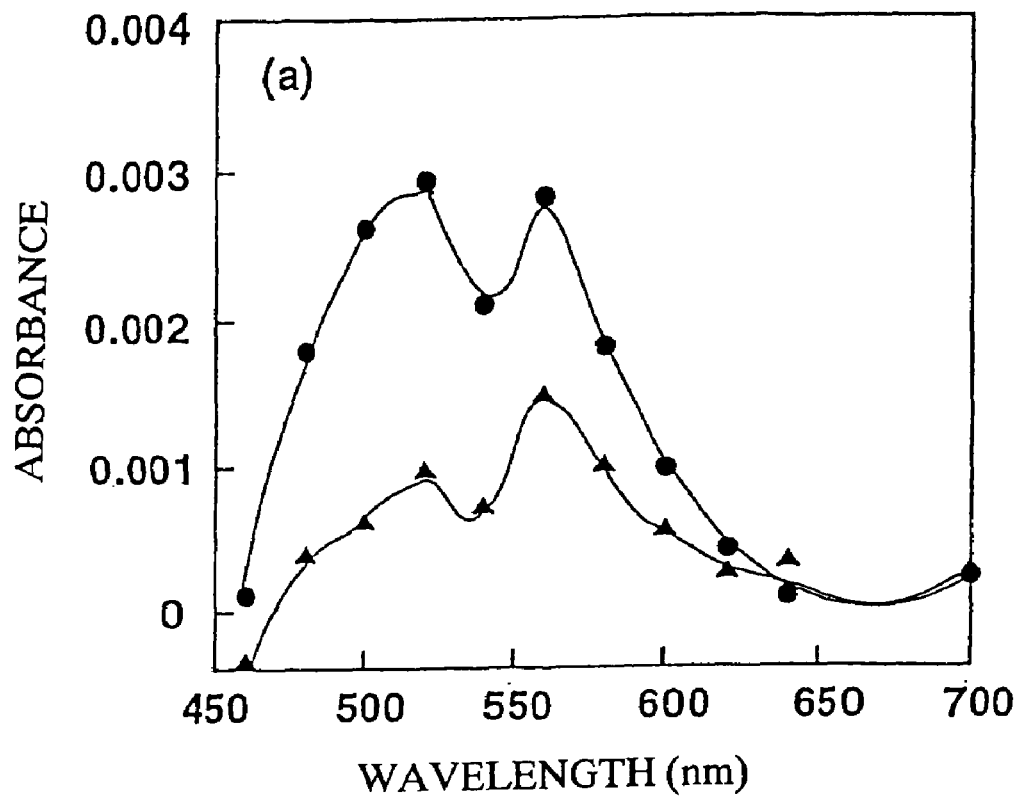
FIG. 7(a) is transient absorption spectrum observed in the photochemical reaction of the Fl-2Sc(OTf)$_3$ complex formed between Fl and Sc(OTf)$_3$ at 25 μs (symbol: ○) and 250 μs (symbol: Δ)
FIG. 7(b) is a visible absorption spectrum in the photoelectron transfer reduction of Fl by (BNA)$_2$ at 5 μs (broken line) and 120 μs (solid line).
Figure 7:
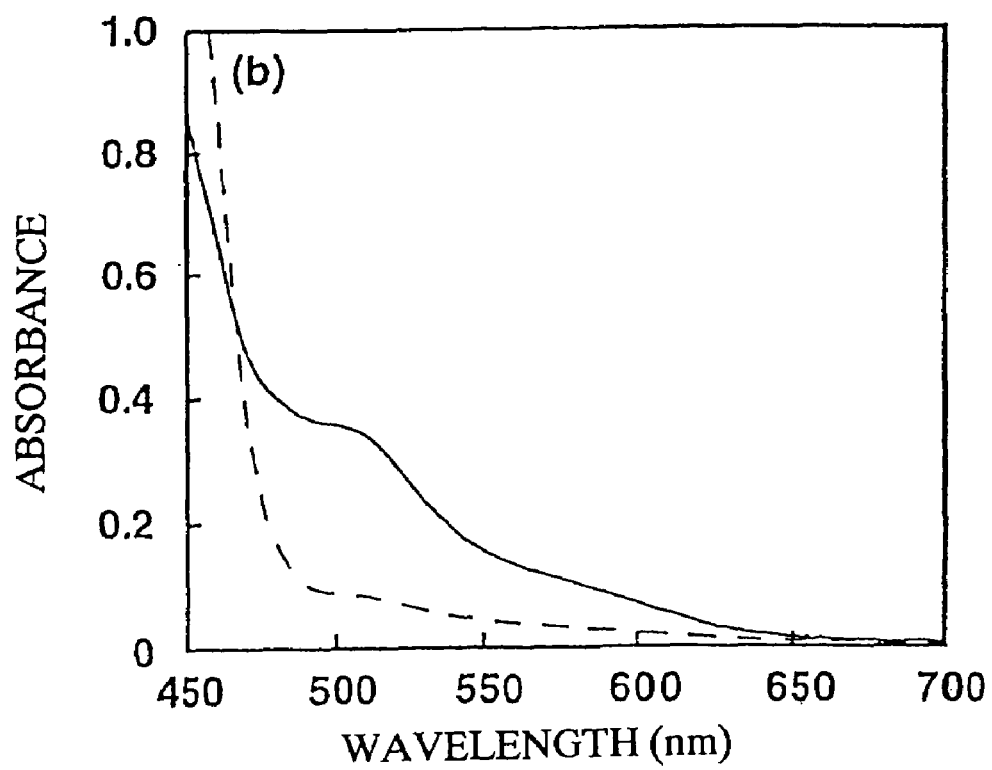

The transient absorption spectra in the visible region ($\lambda_{max}$=560 nm) are observed by the laser flash photolysis of a deaerated MeCN solution containing Fl, Sc(OTf)$_3$ and p-chlorobenzyl alcohol with a 440 nm laser beam as shown in FIG. 7(a).

In order to assign the absorption bands in FIG. 7(a), the photoinduced electron transfer reaction was carried out from a dimeric 1-benzyl-1,4-dihydronicotinamide [(BNA)$_2$] to Fl in the presence of Sc(OTf)$_3$ in MeCN. The (BNA)$_2$ has been known to act as a two electron donor, and radical anions of electron acceptors are formed.

The absorption spectrum assigned to Fl$^{\bullet-}$-2Sc$^{3+}$ is shown in FIG. 7(b), wherein the absorption band at 510 nm is red shifted as compared to the reported band of the radical anion of N(10)-isobutyl-N(3)-methyl flavin ($\lambda_{max}$=478 nm).

Figure 8:
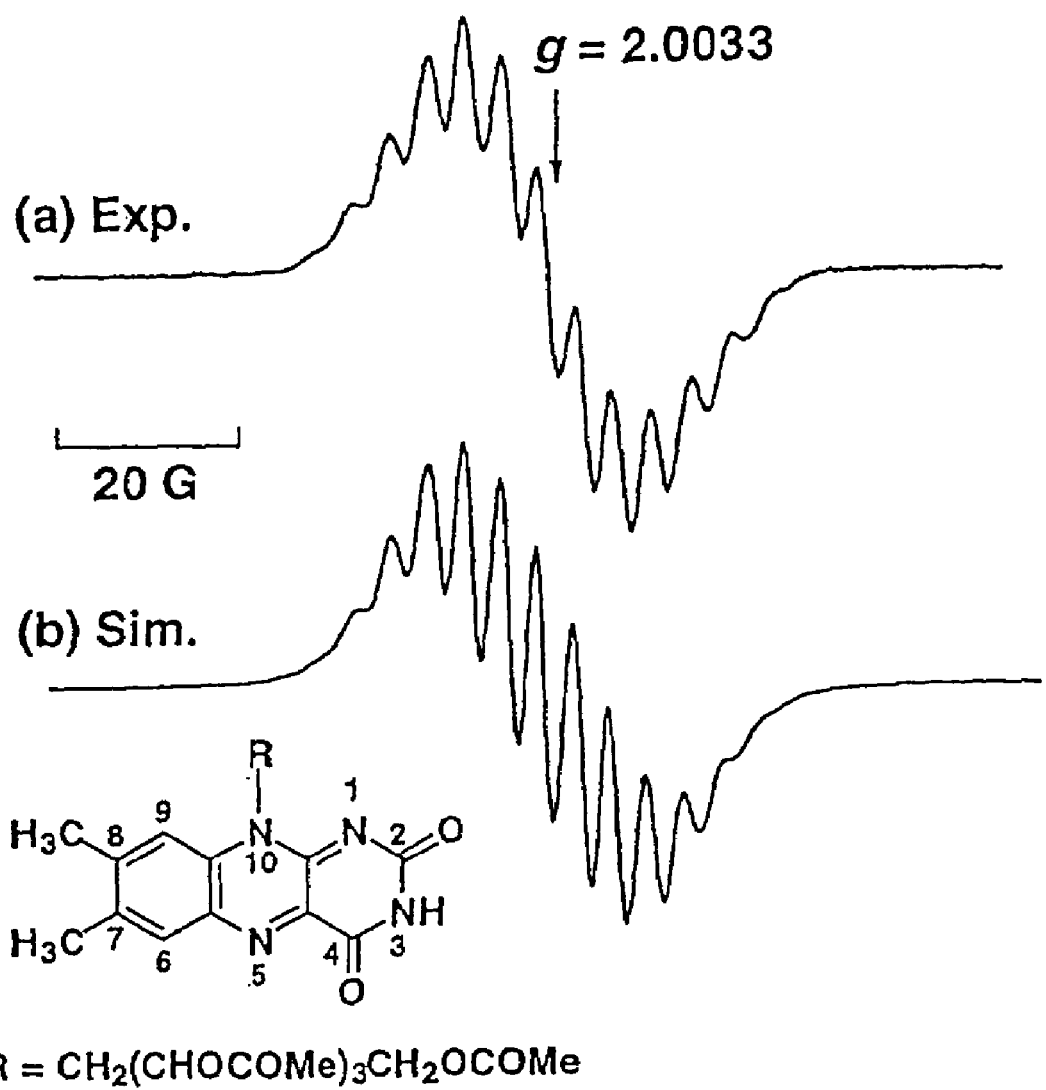
FIG. 8(a) is an ESR spectrum of Fl$^{\bullet-}$-2Sc$^{3+}$ generated in the reaction of Fl with (BNA)$_2$.
FIG. 8(b) is an ESR spectrum by computer simulation.

The formation of Fl$^{\bullet-}$-2Sc$^{3+}$ is confirmed by the ESR spectrum as shown in FIG. 8(a) which exhibits apparent 13 line signals centered at g=2.0033. The hyperfine coupling constants are determined as given in FIG. 8(b) by the computer simulation of the ESR spectrum.

A slightly different ESR spectrum from Fl$^{\bullet-}$ which was produced by photoinduced electron transfer from (BNA)$_2$ to Fl was obtained in the absence of Sc$^{3+}$ ion in MeCN.

The ESR spectrum of Fl$^{\bullet-}$ is essentially the same as that reported for the radical anion of N(10)-isobutyl-N(3)-methyl flavin which exhibits apparent 12 line signals centered at g=2.0038.

The spin densities of the radical anion of N(10)-methyl flavin were calculated using density functional theory at the Becke 3LYP/6-311++G** level as shown in FIG. 8(b). Since there is essentially no spin density on the carbonyl oxygen which can bind with Sc$^{3+}$, the ESR spectrum of Fl$^{\bullet-}$-2Sc$^{3+}$ is only slightly different from that of Fl$^{\bullet-}$.

The transient absorption in FIG. 7(a) ($\lambda_{max}$=560 nm) is clearly different from the transient absorption of Fl$^{\bullet-}$-2Sc$^{3+}$ ($\lambda_{max}$=510 nm) or the transient absorption of Fl$^{\bullet-}$ ($\lambda_{max}$=478 nm).

The absorption bands in the long wavelength region of 500 to 600 nm are very similar to those reported for the neutral radical (FlH$^{\bullet}$). Therefore, the transient absorption band at $\lambda_{max}$=560 nm in FIG. 7(a) may be identified as being due to FlH$^{\bullet}$-2Sc$^{3+}$ which is produced by proton transfer from p-ClC$_6$H$_4$CH$_2$OH+ to Fl$^{\bullet-}$-2Sc$^{3+}$. The absorption band at 520 nm observed at 25 μs after the laser excitation may be overlapped with that assigned to Fl$^{\bullet-}$-2Sc$^{3+}$ ($\lambda_{max}$=510 nm).

Based on the results and discussion described above, the reaction mechanism for the photooxidation of p-chlorobenzyl alcohol by Fl$^{\bullet-}$-2Sc$^{3+}$ is shown in Scheme 1.

Scheme 1

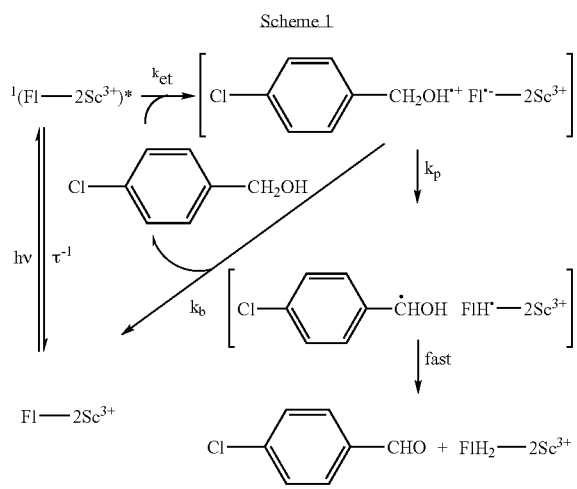

The excited state $^1(Fl\text{-}2Sc^{3+})^*$ is quenched by electron transfer from p-chlorobenzyl alcohol ($k_{et}$) to give a radical ion pair [p-ClC$_6$H$_4$CH$_2$OH$^{\bullet+}$Fl$^{\bullet-}$-2Sc$^{3+}$] in competition with the decay to the ground state.

Next, the proton transfer from p-chlorobenzyl alcohol radical cation to Fl•⁻-2Sc³⁺ occurs in the radical ion pair to give a radical pair [p-ClC₆H₄CHOH•FlH•⁻-2Sc³⁺] as observed in the transient spectrum in FIG. 7(a).

By the hydrogen transfer from p-ClC₆H₄CHOH• to FlH•⁻-2Sc³⁺, products p-ClC₆H₄CHO and FlH₂-2Sc³⁺ are obtained. The proton transfer step ($k_p$) may compete well with the back electron transfer step to the original reaction pair ($k_b$).

By applying the steady-state approximation to the reactive species, ¹(Fl-2Sc³⁺)* and the radical ions and radical pairs in Scheme 2, the dependence of Φ on the p-chlorobenzyl alcohol concentration [p-ClC₆H₄CH₂OH] can be expressed by the equation (14), which agrees with the equation (12) obtained experimentally.

$$\Phi = [k_p/(k_p+k_b)] k_{et} \tau [p\text{-ClC}_6\text{H}_4\text{CH}_2\text{OH}] \div (1 + k_{et} \tau [p\text{-ClC}_6\text{H}_4\text{CH}_2\text{OH}]) \quad (14)$$

The limiting quantum yield $\Phi_\infty$ corresponds to $k_p/(k_p+k_b)$. Therefore, the $\Phi_\infty$ values of smaller than 1 show the competition of the proton transfer process ($k_p$) with the back electron transfer process ($k_b$).

4. Photocatalytic Oxidation of p-Methoxybenzyl Alcohol by Oxygen

Since the Fl-Lu³⁺ complex gives the largest Φ value (0.17) for the photooxidation of p-methoxybenzyl alcohol in deaerated MeCN, the photocatalytic oxidation of p-methoxybenzyl alcohol by oxygen was carried out using the Fl-Lu³⁺ complex.

When an oxygen-saturated MeCN solution containing p-methoxybenzyl alcohol (3.0×10⁻³ M), Lu(OTf)₃ (1.0×10⁻² M) and a catalytic amount of Fl (2.0×10⁻⁴ M) was irradiated with the visible monochromatized light (λ=430 nm), with an increase in the concentration of p-methoxybenzaldehyde and H₂O₂, the reaction proceeded as shown by the equation (15):

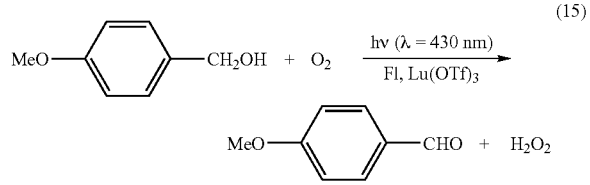

(15)

so that the concentration of p-methoxybenzyl alcohol was reduced.

Figure 9:
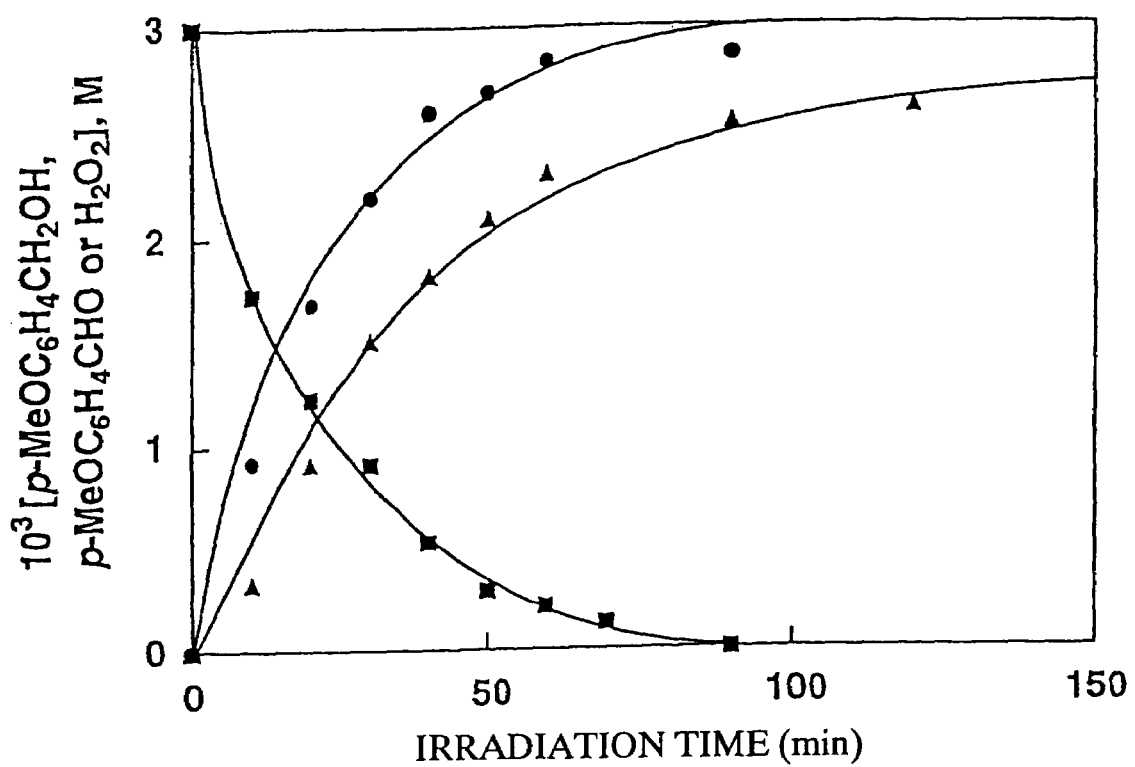
FIG. 9 is a graph showing the change in concentration of p-MeOC$_6$H$_4$CH$_2$OH (symbol: □), p-MeOC$_6$H$_4$CHO (symbol: ○) and H$_2$O$_2$ (symbol: Δ), with respect to the irradiation time for the photooxidation of p-MeOC$_6$H$_4$CH$_2$OH with oxygen using Fl as a photocatalyst.

When irradiated with the light for 50 minutes, yields of p-methoxybenzaldehyde based on the initial amount of Fl exceeded 1400%, so that it is shown that Fl can be efficiently regenerated and recycled in the photooxidation of p-methoxybenzyl alcohol as shown in FIG. 9.

Therefore, Fl acts as an efficient photocatalyst for the oxidation of p-methoxybenzyl alcohol in the presence of Lu(OTf)₃ and oxygen.

The amount of H₂O₂ formed by the photooxidation of p-methoxybenzyl alcohol is somewhat smaller than that of p-methoxybenzaldehyde due to the decomposition of H₂O₂ during the photochemical reaction.

In contrast with the efficient photocatalysis in the presence of Lu(OTf)₃, the photodegradation of photocatalyst (Fl) occurs in the presence of Mg(OTf)₂, so that the yields of H₂O₂ as well as p-methoxybenzaldehyde become very low. It can be seen from this fact that Lu(OTf)₃ can not only act as an efficient co-catalyst in the photooxidation of p-methoxybenzyl alcohol using Fl as a catalyst but also prevents Fl from the photodegradation.

The quantum yield (Φ) of the photocatalytic oxidation of p-methoxybenzyl alcohol by oxygen in the presence of Fl-Lu³⁺ was determined from the rate of formation of p-methoxybenzaldehyde. The Φ value for the photooxidation of p-methoxybenzyl alcohol by Fl-Lu³⁺ in oxygen-saturated MeCN increases with increasing the concentration of p-methoxybenzyl alcohol to reach a constant value $\Phi_\infty = 0.17$ at [p-MeOC₆H₄CH₂OH]=2.7×10⁻² M, which agrees with the corresponding value (0.17) for the photooxidation of p-methoxybenzyl alcohol by Fl-Lu³⁺ in deaerated MeCN (Table 5). From the agreement, since the oxidation of the reduced flavin, FlH₂-Lu³⁺ by oxygen to regenerate Fl-Lu³⁺ is very fast, the oxidation does not affect the Φ value as shown in Scheme 2.

Scheme 2

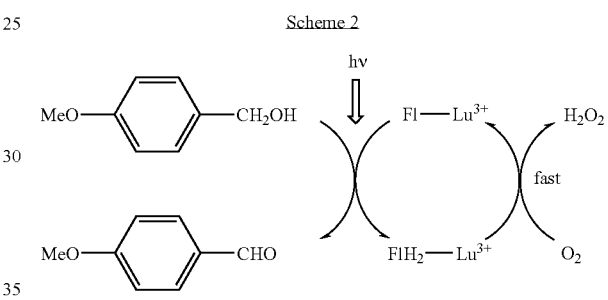

As reported for the Mg²⁺-catalyzed oxidation of reduced flavin by oxygen, the rare-earth metal ion may accelerate the oxidation of the reduced flavin by oxygen, to form H₂O₂. Although the triplet excited state of Fl is quenched by oxygen that is a well-known triplet quencher, the Fl-metal ion complexes can act as efficient and stable photocatalysts in the photooxidation of benzyl alcohol derivatives by oxygen due to the change in the spin state from the n,π* triplet to the π,π* singlet excited state by the complexation with metal ions (see FIG. 3).

INDUSTRIAL APPLICABILITY

The photocatalyst of the present invention has a photocatalytic activity far higher than that of flavin, and is excellent in stability as a catalyst.

The invention claimed is:

1. A photocatalyst comprising a 1:2 complex of flavin with scandium ion.

2. The photocatalyst according to claim 1, wherein the flavin is riboflavin-2',3',4',5'-tetraacetate.

* * * * *